United States Patent [19]

Atkinson et al.

[11] 4,342,827
[45] Aug. 3, 1982

[54] PRODUCTION OF ENZYMES

[75] Inventors: Anthony Atkinson, Salisbury; Christopher J. Bruton, Kew, both of England; Michael J. Comer, Weilheim, Fed. Rep. of Germany; Richard J. Sharp, Salisury, England

[73] Assignee: Public Health Laboratory Service, Center for Applied Microbiology & Research, Salisbury, England

[21] Appl. No.: 41,481

[22] Filed: May 22, 1979
(Under 37 CFR 1.47)

[30] Foreign Application Priority Data

May 22, 1978 [GB] United Kingdom .............. 21194/78

[51] Int. Cl.$^3$ ...................... C12Q 1/32; C12N 15/00; C12N 9/04; C12N 1/20
[52] U.S. Cl. .................................... 435/26; 435/172; 435/188; 435/190; 435/253; 435/832
[58] Field of Search ................. 435/26, 190, 253, 832, 435/172, 188

[56] References Cited

PUBLICATIONS

Sidney P. Colowick and Nathan O. Kaplan, Methods in Enzymology, vol. 1, Academic Press Inc., Publisher, pp. 397–400; 1955.

Thomas E. Bowman, Enzyme Handbook, vol. 1, p. 29, 1969.

R. E. Buchanan and N. E. Gibbons, Co-Editors, Bergey's Manual of Determinative Bacteriology, The William and William Company, pp. 539–540; 1974.

Primary Examiner—Robert J. Warden
Attorney, Agent, or Firm—Stevens, Davis, Miller & Mosher

[57] ABSTRACT

Glycerol dehydrogenase enzymes having exeptionally good thermal stability are produced by culturing novel strains of Bacillus stearothermophilus. Procedures for deriving and identifying suitable strains are described. The strains are grown in conventional culture media, preferably containing 0.05 to 4.0%, especially 0.1 to 1.0%, by weight of glycerol or a glycerol analogue at 40°–65° C. and pH 5 to 8. The enzyme is isolated by conventional cell disruption and separation techniques, and typically has a molcular weight of 240,000±30,000, composed of four similar sub-units, and a specific activity of greater than 5 Units per mg protein at 30° C. by the modified assay described. They may be stored as aqueous solutions or a freeze dried solids.

The enzymes may be used for assay of serum triglycerides by conventional assay methods, but preferably by the nictotinamide adenine dinucleotide spectrophotometric assay at a pH of 7 to 8.8. The pH is preferably controlled by an amine, especially triethanolamine/HCl, buffer.

27 Claims, No Drawings

PRODUCTION OF ENZYMES

The invention relates to improved glycerol dihydrogenase enzymes and to processes for their production.

Glycerol dehydrogenase (GDH) enzymes are useful in biochemical assays, such as the assay of serum triglycerides for clinical diagnosis, and also for the production of dihydroxyacetone for cosmetic manufacture. However relatively few sources of GDH are known and all such enzymes previously known and used have been extremely unstable having half-lives in solution at ambient temperatures of less than 2 days. Even as freeze-dried powders storage at low temperature has been advocated.

It has now been found that certain thermophilic micro-organisms produce GDH enzymes which are stable in solution for long periods at ambient or even elevated temperatures.

According to the present invention, therefore, there is provided a glycerol dehydrogenase enzyme preparation having an active half-life of greater than 4 days when stored at 20° C. as a 3 mg/ml solution in a pH 6.8 buffer solution comprising 50 mM potassium phosphate, 10 mM β-mercapto-ethanol and 0.1 mM phenylmethyl sulphonyl fluoride (PMSF). Such enzymes are hereinafter termed "thermostable GDH enzymes".

Glycerol dehydrogenase enzymes in accordance with the invention may be prepared by culturing thermophilic organisms of the strain Bacillus Stearothermophilus RS93 or derivatives or mutants thereof retaining the ability to produce thermostable GDH enzymes followed by cell disruption and separation of the enzyme from cell debris. Examples of such derivatives or mutants include that designated SC7. These strains have been deposited with the National Collection of Industrial Bacteria, Aberdeen, Scotland under the accession numbers NCIB 11400 & NCIB 11401.

They may be identified as follows:

|  | RS93 (NCIB 11400) | SC7 (NCIB 11401) |
|---|---|---|
| Colonial appearance (on TSB agar plates incubated overnight at 60° C.) | Translucent, plane-convex round, smooth and entire with a "salmon" pinkish granular centre and clear edge | As RS93 but pigmentation less marked |
| Genetic characterization | Pro⁻Arg⁻His⁻Nic⁻Thi⁻Bio⁻His⁻Nic⁻Bio⁻ (leaky mutent) | (leaky mutant) |
| Microscopic appearance | Weekly staining gram positive rod, 1.25μ × 0.25μ Spore forming with swollen bacillary body and a subterminal or central oval shaped spore | As RS93 |
| Biochemical tests |  |  |
| Growth at 30° C. | − ve | As RS93 |
| 37° C. | ± ve (slow; 2-3 days) |  |
| 55° C. | + ve |  |
| 60° C. | + ve |  |
| 70° C. | − ve |  |
| (1 days incubation) |  |  |

| Fermentation of: | Day 1 | Day 3 |
|---|---|---|
| Adonitol | w w | + + |
| Aesculin | − − | − − |
| Arabinose | − − | − − |
| Dextrin | − − | − − |
| Dextrose A/G | w w | w w |
| Dulcitol | − − | − − |
| Erythritol | − − | − − |
| Galactose | − − | − − |
| Glycerol | + + | + + |
| Glycogen | − − | − − |
| Inositol | w w | w w |
| Inulin | − − | − − |
| Lactose | − − | − − |
| Laevulose | − − | w w |
| Maltose | − − | − − |
| Mannose | w w | w w |
| Raffinose | − − | − − |
| Rhamnose | − − | − − |
| Saccharose | + w | + + |
| Salicin | − − | − − |
| Starch | − − | − − |
| Sorbitol | w − | w w |
| Trehalose | − − | w w |
| Xylose | − − | − − |
| Mannitol | + w | + + |

Growth in peptone+water at 60° C. for 24 hours showed a tolerance to sodium chloride up to a final concentration of 5% (w/v) NaCl Production of
Catalase: +
Oxidase: +
Nitrate reductase: −
Nitrite reductase: −

The strains may be further recognised by production of a bacteriocin capable of inhibiting growth of Bacillus stearothemophilus NCIB 11270 (or other thermophilic Bacilli) according to the following test:

Dilution plates are prepared containing approximately 10 to 20 colonies/plate and incubated overnight. The colonies produced are killed by exposure to chloroform vapour for two hours and the plates are then vented to remove chloroform. They are "overseeded" with a suspension of NCIB 11270 dense enough to form a mat growth and incubated overnight at 60° C. Single dead colonies of RS93 or SC7 are surrounded by a clear zone of no-growth in the mat formed by NCIB 11270. The bacteriocin factor causing this inhibition has been termed thermocin and has been shown to be a thermostable glycoprotein with a molecular weight of about 13,000 daltons.

The strains contain a plasmid of size about 3 million daltons believed to code for this thermocin.

Derivatives and mutants retaining the GDH-producing ability may be prepared by standard techniques such as environmental pressure or may occur spontaneously during culture. They may be identified by incubation with propane-1,2-diol (a substrate for GDH, but not for glycerokinase more commonly produced by thermophilic bacilli) and chloramphenicol, followed by staining with triphenyl tetrazolium chloride.

These strains and derivatives or mutants thereof, will generally produce GDH enzyme even in a medium which lacks glycerol or glycerol analogue. However for maximum yield the culture medium will normally contain at least 0.05% by weight of glycerol or glycerol analogue though preferably less than 4.0% by weight. Most preferably the culture medium will contain 0.1% to 1.0% by weight of glycerol or glycerol analogue.

The term glycerol analogue as used herein encompasses poly-functional $C_3$ alcohols, especially those containing two hydroxy groups, for example glyceric acid, L- or D-glyceraldehyde, dihydroxy acetone, 3-mercaptopropane-1,3-diol, propane-1,3-diol or propane-1,2-diol.

The culture medium in either case may be a complex medium containing naturally-derived nutrient sources, such as peptones, yeast hydrolysates beef extract, casein hydrolysates etc. or a defined salts medium containing inorganic and simple organic nutrient sources.

The culture is preferably conducted at a temperature at which the organism will grow, typically 40°–65° C., more especially from 50° to 65° C. and at a pH of from 5 to 8. It may be conducted under either aerobic or anaerobic conditions, though the former condition is preferred. It appears that there may be an optimum culture period after which the yield may fall. The optimum period will depend on the strain and culture conditions used and must be determined by experiment. Periods of 10 to 20 hours have, however, been found suitable.

The cell disruption may be carried out by conventional techniques such as sonication, homogenisation or treatment with enzymes. Conventional enzyme isolation and purification techniques may then be used, for example ion-exchange chromatography, fractionation on calcium phosphates, precipitation with ammonium sulphate or an organic solvent (eg ethanol at 10 to 20% Volume/Volume concentration) gel filtration on dextrans, ararose or agarose-polyacrylamide and/or affinity chromatography on immobilized nucleotide derivativised matrices, or on immobilized sulphonic acid substituted chlorotriazinyl ("Procion"-Trade Mark) dyes.

The thermostable GDH enzymes produced from the strains of *Bacillus stearothermophilus* described above typically have a structure composed of four identical or similar sub-units each of molecular weight about 60,000 giving an overall molecular weight of about 240,000±30,000 daltons. When homogeneous and tested by the assay method described below they have a specific activity of at least 5 and normally about 10 to 30 units per mg protein at 30° C. and pH 8.5. When tested under similar conditions against analogous substrates the activities (Vmax) relative to glycerol (100%) were:

| | | |
|---|---|---|
| 3-mercapto-propane1, 3 diol | 49% | |
| propane1, 3diol | 16% | |
| propane1, 2 diol | 165% | |
| dihydroxyacetone | <10% | cannot be measured accurately due to blank. |
| glyceric acid | <10% | |

The activity is inhibited by high concentrations of $NH_4^+$ ions. The enzymes should preferably be purified at low temperatures (about 4° C.) to avoid destruction by proteases, but when purified they are preferably stored at room temperature.

The enzyme preparations of the invention may be crude cell extracts, or partially or highly purified preparations. They may be supplied as freeze dried or other solid forms or as aqueous solutions which may contain from 0.1 to 50 Units/ml according to the level of glycerol to be assayed.

The enzyme preparations may be used to estimate glycerol or glycerol analogues, either present as such or released from glycerides by alkaline hydrolysis or enzyme (eg lipase) action, in a wide variety of samples including sera and culture media.

According to a further aspect of the invention, a process for estimating glycerol or a glycerol analogue in a sample comprises mixing the sample with a glycerol dehydrogenase enzyme preparation and nicotinamide adenine dinucleotide (NAD) in a buffer solution at a pH of at least 7 and preferably 8 to 8.8 and measuring the increase in optical density at or about 340 nm. The glycerol is then estimated by comparing either the rate of increase in optical density or the final optical density with that produced by a standard solution. Where the rate of increase ($\Delta OD_{340}$) is used, the sample and standard should preferably be diluted to give a value of $\Delta OD_{340}$ in the range 0.06 to 0.12 per minute.

The assay proceeds as in the equation

$$\text{Glycerol} + \text{NAD} \xrightarrow{\text{GDH}} \text{Dihydroxyacetone} + \text{NADH}$$

Previous assays based on this reaction have suffered from inaccuracies due to autocatalysis since at the higher pH used (at least 9, normally 10–11) dihydroxyacetone forms a enol dimer which catalyses chemical reduction of NAD unrelated to the enzyme. In the present assay autocatalysis is avoided by use of a lower pH. Moreover it has been found that the buffer system influences the rate of this side reaction. Hence the buffer is preferably an amine, especially a triethanolamine/HCl buffer although other buffers such as phosphate may be used. Carbonate/bicarbonate buffers can be used, but are less suitable. Free ammonium ions should be avoided due to the inhibitory effect noted above.

The enzyme preparations of the invention may thus conveniently be presented as part of a test kit containing the enzyme as a dried, normally freeze-dried powder or an aqueous solution and also a buffer solution of pH 8 to 8.8 and a solution of nicotinamide adenine dinucleotide (NAD). The kit may also optionally contain a standard glycerine solution and either alkaline KOH or a lipase solution to release free glycerine from glycerides.

Where the enzyme is present as an aqueous solution, its concentration may vary widely from 0.1 to 50 Units/ml depending on the intended use of the kit and more than one enzyme solution may be provided to cover differing glycerol levels in the sample. The buffer is preferably an amine, especially a triethanolamine buffer and preferably has a pH about 8.5. The NAD solution may be of any appropriate concentration, typically 10 mg/ml.

Typical embodiments of the various aspects of the invention will now be described by way of example only. In these examples the media used were as follows:

| *Bacillus stearothermophilus* (BS) medium | g/l |
|---|---|
| Tryptic meat digest (Bacto tryptone) | 20 |
| Yeast extract | 10 |
| $FeCl_3.6H_2O$ | 0.014 |
| $MnCl_2.4H_2O$ | 0.03 |
| $K_2SO_4$ | 2.6 |
| $MgSO_4.7H_2O$ | 0.54 |
| Citric Acid | 0.64 |
| $Na_2HPO_4.2H_2O$ | 6.4 |
| Modified BS medium | g/l |
| As above except: | |
| Tryptone | 2.0 |
| Yeast extract | 50 |
| $K_2SO_4$ | 6.0 |
| Antifoam agent (RD Antifoam) | 2.5 |
| pH adjusted to 7.1 ± 0.1 with 10N.NaOH | |

TSB agar

This contained (in grams per liter): Tryptone (Oxoid L42), 17.0; Soya Peptone (Oxoid L44), 3.0; Glucose, 2.5; NaCl, 5.0; $K_2HPO_4$, 2.5; and Agar (Oxoid No: 1), 15.0. The final pH was 7.3.

CCl Medium

This contained (in grams per liter): $NaH_2PO_4 2H_2O$, 3.12; $NH_4Cl$, 5.04; KCl, 0.37; $Na_2SO_4.10H_2O$, 3.22; Citric acid monohydrate, 0.42; ZnO, 0.002; $FeCl_3 6H_2O$, 0.027; $MnCl_2.4H_2O$, 0.01; $CuCl_2 2H_2O$, 0.00085; $CoCl_2.6H_2O$, 0.0024; $H_3BO_3$, 0.00031; MgO, 0.05; $CaCO_3$, 0.01 and $Na_2MoO_4.2H_2O$, 0.0024, dissolved in HCl (final concentration 0.295 ml conc acid per liter of medium) and adjusted to pH 7.3.

The basic strain used was that designated RS93 (deposited as NCIB 11400). Derivative strains were produced as follows:

Several dilution plates on TSB agar were prepared from a 200 ml shake flask liquid culture of RS93 in BS medium containing 0.4 g/100 ml glycerol incubated at 60° C. and 150 rpm overnight in an orbital incubator. Replicate plates of dishes containing 50 to 100 colonies were made using a velvetine pad. The original plates were then "killed" by exposure to chloroform vapour for 2 hours. These were then overseeded with sloppy agar containing a suspension of B. caldolyticus with sufficient concentration to produce a mat growth when incubated overnight at 60° C. The replicate plates were also incubated at 60° C. overnight then sprayed with an aqueous solution of 1% (v/v) 1,2-propanediol and 1.5% (w/v) chloramphenicol. The plates were then incubated for a further hour at 60° C. then sprayed with a 10% solution of tri-phenyl tetrazolium chloride in 1 M potassium phosphate buffer pH7.5.

The "killed" and replicate plates were compared and single colonies with the largest zones of inhibition and staining a deep pink colour were transferred from replicates to fresh plates then incubated overnight. Suspensions made from these plates in normal saline were innoculated into 200 ml BS medium containing 4% (v/v) glycerol incubated at 60° C. and 150 r.p.m. on a shaker overnight (16 hours). Cells were harvested by centrifuging at 13,000 g for 20 minutes at 4° C., suspended in 100 ml 100 mM Tris-HCl pH7.5 containing β-mercapto-ethanol and PMSF and again centrifuging at 13,000 g for 20 minutes. A second wash of 50 ml using the same buffer was done then the cells were suspended in 20 ml of 100 mM Tris-HCL pH 7.5 as above and sonicated for 2×1 minutes with samples kept as cool as possible in an ice bath. Each sample was checked for GDH activity and dry weight. The isolate giving the highest activity and cell mass was retained and designated SC7 (NCIB 11401).

Mutants retaining the GDH producing ability may be generated by conventional environmental pressure techniques and can be shown to produce the enzyme as described above.

In a typical mutation experiment a sample of BS medium used to grow strain SC7 was subjected to amino acid analysis. This showed that the strain metabolized principally the amino acids aspartic acid, glutamic acid alanine, serine and glycine. Accordingly CCl Medium was made up to contain 5 mM of each of these amino acids except serine and glycine which were 2 mM and 1 mM respectively supplemented with biotin (1 mg/liter) and glycerol (2 g/liter). After several serial transfers of SC7 through this medium it was noted that a morphological mutant was arising when the culture was plated onto TSB agar. Single colonies were isolated and shown to produce GDH although a high rate of reversion to SC7 morphology on culturing in BS medium made estimation of yield difficult.

Assay method

Assays for GDH activity were carried out by the following procedure and all references to activities in the present description and claims refer to activity as measured by this assay.

Basic reagents:
  (i) 0.25 M Triethanolamine-HCl (pH 8.5).
  (ii) 1 M Glycerol
  (iii) 10 mg/ml NAD (nicotinamide adenine dinucleotide)

600 µl, $H_2O$, 200 µl triethanolamine-HCl solution, 25 µl NAD solution and 5 to 200 µl of the sample to be assayed were mixed in a cuvette (pathlength 1 cm.). After pre-equilibration to attain 30° C., 100 µl of glycerol solution was added to initiate the reaction.

The reduction of NAD was followed by spectrophotometric means, by observing the absorbance of the solution at 340 nm. Either a water or reagent blank was used, and units were expressed as µmoles of NADH formed per minute at 30° C. with dilution to give $\Delta OD_{340}$ in the range 0.06 to 0.12 per minute.

By way of comparison, the procedure was repeated with 50 µl sample (about 0.5 U/ml) and with 50 µl 0.5 M dihydroxyacetone without enzyme (to determine the blank) in triethanolamine phosphate and carbonate/bicarbonate buffers at pH 8, 8.5, 9 and 9.5. Results ($OD_{340}$) are shown in Table 1.

TABLE 1

| Solution | Buffer | $\Delta OD_{340}$ | | | |
|---|---|---|---|---|---|
| | | pH 8 | pH 8.5 | pH 9 | pH 9.5 |
| Dihydroxyacetone 50 µl 0.5M | carbonate/bicarbonate | 0 | 0.31 | 0.36 | 0.94 |
| | phosphate | 0 | 0.17 | 0.34 | 0.63 |
| | triethanolamine/HCl | 0 | 0.03 | 0.21 | 0.48 |
| Sample 50 µl 0.52 U/ml | phosphate | 0.49 | 0.54 | — | — |
| | tirethanolamine/HCl | 0.39 | 0.49 | — | — |

From this it can be seen that the "blank" is much reduced at lower pH and in triethanolamine buffer. Sample response is reduced at lower pH, but is still adequate at pH 8.

EXAMPLE 1

B. stearothermophilus RS 93 was grown in 100 ml of the BS medium (as described above) containing 4 g/l of glycerol in a 400 ml flask shaken at 200 rpm for 12–16 hours at 60° C. The resulting cell material was collected and assayed for GDH activity. The yield of enzyme was 8 units/g dry cells, representing 0.03 U/ml of culture.

EXAMPLE 2

The culture of Example 1 was repeated in the absence of glycerol when the yield of enzyme was 2 units/g dry cells (0.01 U/ml culture).

EXAMPLES 3 AND 4

Examples 1 and 2 were repeated using the strain *B. stearothermophilus* SC 7. The yields were 0.14 U/ml culture and 0.03 U/ml culture respectively.

EXAMPLE 5

A 1 liter seed culture of *B. stearothermophilus* SC 7 was prepared at 60° C. in a stirred BS medium containing 4 g/l of glycerol. This was used to seed a similar 20 liter seed culture.

A 400 liter culture vessel containing 400 liters of modified BS medium without glycerol at 60° C. was seeded with the 20 liter seed culture. Growth was continued at 60° C. and a controlled pH of 7.0±0.2 with aeration at 300 liters of air per minute and stirring at 250 rpm until the culture had an optical density of 0.8.

20 liters of 500 g/l aqueous glycerol were added at a rate of 1.5 to 1.6 liter per hour when the optical density at 600 nm reached 1.3 to 1.4. After 19 hours total culture time the culture was cooled to ambient temperature and the cells havested in a De Laval centrifuge. The cells were washed with phosphate buffer ($KH_2PO_4$ 534 g/$Na_2HPO_4$ 761 g made up to 2001).

The total final yield of cells was about 16 Kg wet (4 Kg dry) giving a specific activity of 8.0 U/g wet cells (35 U/g dry cells) and a total yield of 128,000 units per 4001 culture.

EXAMPLE 6 (PURIFICATION)

40 g of the wet cell paste of *B. stearothermophilus* RS93 was suspended in 150 ml. 40 mM potassium phosphate (KP), (pH 6.8). The cells were disrupted by sonication at 20 K cycles/sec for 5×1 minutes. Cell debris was removed by centrifugation at 30,000 g for 20 minutes. The cell extract was chromatographed on DEAE-cellulose (DE52; Whatman Biochemicals) which had been freshly pre-equilibrated in 40 mM KP (pH 6.8). The cell extract was loaded onto a 110 ml column (14×3.2 cm) at 60 ml/hr and the enzyme was eluted with an 800 ml linear phosphate gradient from 40 to 400 mM KP (pH 6.8) at 25 ml/hr. Glycerol dehydrogenase was eluted between 150 and 250 mM phosphate. Active fractions were pooled and dialysed against 10 mM KP (pH 6.8). The active pool was then loaded onto a 50 ml (6×32 cm) triazine dye—agarose column (as described, for example, in U.K. patent application No. 3505/78) at 100 ml/hr; the column consisted of either Procion (Trade Mark) Red HE-3B or Procion Red HE-7B (derivatives of Procion Red, Colour Index No C118159) linked to Sepharose 4B (Trade Mark) at 1.0–2.0 mg dye/g Sepharose (as described in U.K. Patent Specification No. 3505/78). The column was washed with 200 ml 10 mM KP (pH 6.8) and the enzyme was eluted with 100 ml 1 M KCl in 10 mM KP (pH 6.8).

Alternatively glycerol dehydrogenase could be absorbed onto Procion Green HE-4BD/Sepharaose 4B or Procion Red HE-3B/Sepharose 4B at an ionic strength of 10 mM KP at pH 6.8 or 7.5 respectively. After washing the column with the buffer the enzyme could be eluted with 10 mMKP, pH 6.8 or 7.5 respectively, also containing 4 mM NAD. Active enzyme was pooled and concentrated on an ultrafiltration membrane (Amicon flatbed PM 10) to a volume of 5 ml. The concentrated enzyme was then loaded onto a 500 ml column (100×2.5 cm) of a cross linked agarose-polyacrylamide copolymer for gel filtration. (Ultrogel AcA 34 supplied by LKB; Sweden) at 9 ml/hr. The column was eluted with 50 mM KP (pH 6.8), and glycerol dehydrogenase of molecular weight 240,000±30,000 was collected. SDS polyacrylamide gel electrophoresis of the pooled active fractions revealed a single protein band at 58,000±5,000. The final pure enzyme had a specific activity of 5 to 10 U/mg. Typical specific activities at various stages of purification are shown in Table 2.

TABLE 2

|  | Units | Specific Activity (U/mg) |
| --- | --- | --- |
| Cell Extract | 94 | 0.03 |
| DE 52 Pool | 73 | 0.23 |
| Procion-Sepharose Pool | 65 | 2.1 |
| ACA 34 Pool | 55 | 7.8 |

EXAMPLE 7

Example 6 was repeated using wet cell paste of the strain SC 7 (Example 5). The resulting specific activities are shown in Table 3.

EXAMPLE 8

The enzyme was found to bind to freshly suspended DEAE cellulose, but not to older samples of DEAE cellulose or to DEAE dextran gel (Sephadex-Trade Mark). Hence Example 7 was repeated except that instead of the DEAE-cellulose, the cell extract was diluted with 30 mM KP, pH 7.5 and passed at 60 ml/min down a 110 ml column of DEAE-dextran gel (Sephadex A-50-Pharmacia) which had been pre-equilibrated in 30 mM KP, pH 7.5.

The active enzyme solution passing through the column was then loaded onto the triazine-agarose column as in Example 6. The resulting specific activities are shown in Table 3.

TABLE 3

|  | EXAMPLE 7 | | EXAMPLE 8 | |
| --- | --- | --- | --- | --- |
|  | Units | Sp Activity (U/mg) | Units | Sp Activity (U/mg) |
| Cell Extract | 280 | 0.07 | 280 | 0.07 |
| DE52/A-50 Pool | 186 | 0.41 | 223 | 0.44 |
| Procion-Sepharose Pool | 170 | 3.9 | 195 | 3.9 |
| ACA 34 Pool | 132 | 10.5 | 162 | 10.9 |

We claim:

1. A glycerol dehydrogenase enzyme preparation having an active half-life of greater than 4 days when stored at 20° C. as a 3 mg/ml solution in a pH 6.8 buffer solution consisting of 50 mM potassium phosphate, 10 mM β-mercaptoethanol and 0.1 mM phenylmethyl sulphonyl fluoride.

2. An enzyme preparation according to claim 1 having a specific activity of at least 5 Units per mg protein at 30° C. and pH 8.5.

3. An enzyme preparation according to claim 1 in the form of an aqueous solution at an enzyme potency of 0.1–50 Units/ml.

4. A solid freeze-dried enzyme preparation according to claim 1.

5. An enzyme preparation according to claim 1 derived from a strain of Bacillus stearothermophilus selected from NCIB 11400, NCIB 11401 and glycerol dehydrogenase producing derivatives and mutants thereof.

6. An enzyme preparation according to claim 5 having a molecular weight of 240,000±30,000 composed of four similar sub-units.

7. A test kit comprising the said enzyme preparation of claim 1.

8. A test kit according to claim 7 wherein the preparation is buffered to a pH of 8 to 8.8.

9. A test kit according to claim 7 wherein the preparation is buffered with an amine buffer.

10. A test kit according to claim 9 wherein the preparation is buffered with triethanolamine/hydrochloric acid.

11. A process for producing the glycerol dehydrogenase enzyme preparation of claim 1 comprising culturing a microorganism having the identifying characteristics of *Bacillus stearothermophilus* NCIB 11400 or NCIB 11401 or a glycerol-dehydrogenase producing derivative or mutant thereof, capable of producing said enzyme, in a culture medium, disrupting the cells and separating the enzyme from the cell debris.

12. A process according to claim 11 wherein the culture medium contains 0.05 to 4.0% by weight of glycerol or glycerol analogue.

13. A process according to claim 12 wherein the culture medium contains 0.1 to 1.0% by weight of glycerol or glycerol analogue.

14. A process according to claim 12 wherein the glycerol analogue is selected from glyceric acid, L- or D-glyceraldehyde, dihydroxy acetone, 3 mercapto-propan 1.3 diol, propan 1.3 diol and propan 1.2 diol.

15. A process according to claim 11 conducted at a temperature of 50° to 65° C.

16. A process according to claim 11 conducted under aerobic conditions.

17. A process according to claim 11 wherein the enzyme is purified by a process including the step of affinity chromatography on an immobilised, sulphonic acid substituted chlorotriazinyl dye.

18. The solid enzyme preparation of claim 1.

19. A test kit comprising a glycerol dehydrogenase enzyme preparation having an active half-life of greater than 4 days when stored at 20° C. as a 3 mg/ml solution in a pH 6.8 buffer solution consisting of 50 mM potassium phosphate, 10 mM $\beta$-mercapto-ethanol and 0.1 mM phenylmethyl sulphonyl fluoride, an aqueous solution of nicotinamide adenine dinucleotide and a buffer solution having a pH of 7 to 8.8.

20. A method of producing a derivative or mutant of *Bacillus stearothermophilus* comprising subjecting at least one of the strains NCIB 11400 and NCIB 11401 to environmental pressure techniques and selecting glycerol dehydrogenase producing strains from the resultant derivative strains.

21. A method according to claim 20 wherein the strains are subjected to environmental pressure by culture in a defined medium also containing serine, glycine, aspartic acid, glutamic acid and alanine.

22. A process for estimating glycerol or a glycerol analogue in a sample comprising mixing the sample with a glycerol dehydrogenase enzyme preparation having an active half-life of greater than 4 days when stored at 20° C., as a 3 mg/l solution in a pH 6.8 buffer solution consisting of 50 mM potassium phosphate, 10 mM $\beta$-mercapto-ethanol and nicotinamide adenine nucleotide in a buffer solution at a pH of 7 to 8.8 and measuring the increase in optical density at or about 340 nm.

23. A process according to claim 22 whwerein the pH is 8 to 8.8.

24. A process according to claim 22 wherein the buffer is an amine buffer.

25. A process according to claim 22 wherein the buffer is a triethanolamine/hydrochloric acid buffer.

26. A biologically pure culture of *Bacillus stearothermophilus*, having the identifying characteristics of NCIB 11400, said culture being capable of producing the glycerol dehydrogenase of claim 1 in a recoverable quantity upon fermentation in a nutrient medium containing assimilable sources of carbon, nitrogen and inorganic substances.

27. A biologically pure culture of *Bacillus stearothermophilus*, having the identifying characteristics of NCIB 11401, said culture being capable of producing the glycerol dehydrogenase of claim 1 in a recoverable quantity upon fermentation is a nutrient medium containing assimilable sources of carbon, nitrogen and inorganic substances.

* * * * *